(12) United States Patent
Jung et al.

(10) Patent No.: US 9,133,526 B2
(45) Date of Patent: Sep. 15, 2015

(54) **COMPOSITION AND KIT FOR DETECTION AND ANALYSIS OF STRAINS OF *CLOSTRIDIUM DIFFICILE* AND METHOD OF DETECTING STRAINS OF *CLOSTRIDIUM DIFFICILE* BY USING THE SAME**

(71) Applicant: Samsung Electronics Co., Ltd., Suwon-si, Gyeonggi-do (KR)

(72) Inventors: Sun-ok Jung, Seongnam-si (KR); Joon-ho Kim, Seongnam-si (KR); Soo-kwan Lee, Seoul (KR); Kyu-youn Hwang, Seoul (KR); Tae-hee Um, Suwon-si (KR)

(73) Assignee: SAMSUNG ELECTRONICS CO., LTD., Suwon-Si (KR)

( * ) Notice: Subject to any disclaimer, the term of this patent is extended or adjusted under 35 U.S.C. 154(b) by 138 days.

(21) Appl. No.: 13/754,609

(22) Filed: Jan. 30, 2013

(65) Prior Publication Data

US 2013/0330720 A1      Dec. 12, 2013

(30) Foreign Application Priority Data

Jun. 8, 2012   (KR) .................. 10-2012-0061671

(51) Int. Cl.
*C12Q 1/68* (2006.01)
*C12P 19/34* (2006.01)

(52) U.S. Cl.
CPC .......... *C12Q 1/689* (2013.01); *C12Q 2600/156* (2013.01)

(58) Field of Classification Search
USPC ........................................ 435/6.12
See application file for complete search history.

(56) References Cited

U.S. PATENT DOCUMENTS

| | | |
|---|---|---|
| 5,459,034 A | 10/1995 | Tabaqchali et al. |
| 8,101,362 B2 | 1/2012 | Cockerill, III et al. |
| 2009/0208948 A1 | 8/2009 | Paquette et al. |
| 2011/0256535 A1 | 10/2011 | Dolinger et al. |
| 2011/0287965 A1 | 11/2011 | Tsang et al. |
| 2012/0028819 A1 | 2/2012 | Van Den Bogaard et al. |

FOREIGN PATENT DOCUMENTS

| | | |
|---|---|---|
| WO | WO 98/45706 A1 | 10/1998 |
| WO | WO 2010/039787 A1 | 4/2010 |

OTHER PUBLICATIONS

Luna et al., "Rapid Stool-Based Diagnosis of *Clostridium difficile* Infection by Real-Time PCR in a Children's Hospital," Journal of Clinical Microbiology, 2011, vol. 49, No. 3, pp. 851-857.*
GenBank Accession No. M65250, publicly available May 2001, retrieved on-line [retrieval date, Nov. 20, 2014; http://www.ncbi.nlm.nih.gov/nuccore/M65250].*
Carman et al., "Glutamate Dehydrogenase Is Highly Conserved among *Clostridium difficile* Ribotypes", *J. Clinical Microbiol.*, 50(4): 1425-1426 (2012).
Zheng et al., "Multicenter Evaluation of a New Screening Test That Detects *Clostridium difficile* in Fecal Specimens", *J. Clinical Microbiol.*, 42(8): 3837-3840 (2004).
European Patent Office, Extended European Search Report in European Patent Application No. 13161660.9, Sep. 3, 2013, 6 pp.

* cited by examiner

*Primary Examiner* — Young J Kim
(74) *Attorney, Agent, or Firm* — Leydig, Voit & Mayer, Ltd.

(57) ABSTRACT

A composition and kit for detecting *Clostridium difficile* including a primer set for detecting a strain of *Clostridium difficile*, and a method of detecting *Clostridium difficile* by using the same.

11 Claims, 10 Drawing Sheets

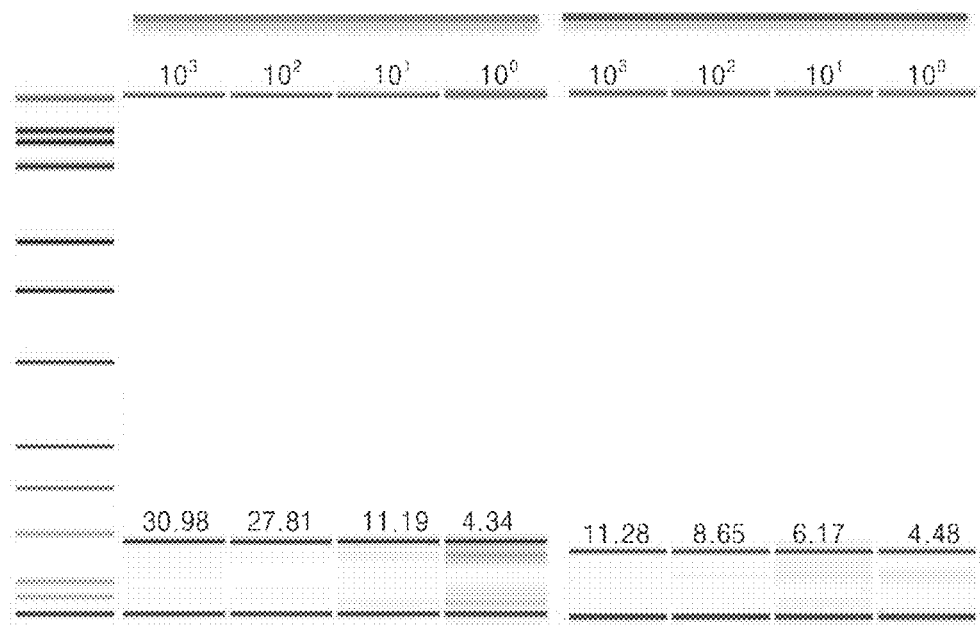

SEQUENCE LISTING

```
<160> NUMBER OF SEQ ID NOS: 30

<210> SEQ ID NO 1
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 1
gctgcattag aaaactctat aac                                              23

<210> SEQ ID NO 2
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 2
cagcctctgg agtagttg                                                    18

<210> SEQ ID NO 3
<211> LENGTH: 17
<212> TYPE: DNA
<213> ORGANISM: Artificial Sequence
<220> FEATURE:
<223> OTHER INFORMATION: synthetic oligonucleotide
<220> FEATURE:
<221> NAME/KEY: modified_base
<222> LOCATION: (4)..(4)
<223> OTHER INFORMATION: LNA
<220> FEATURE:
<221> NAME/KEY: modified_base
<222> LOCATION: (7)..(7)
<223> OTHER INFORMATION: LNA
<220> FEATURE:
<221> NAME/KEY: modified_base
<222> LOCATION: (10)..(10)
<223> OTHER INFORMATION: LNA
<220> FEATURE:
<221> NAME/KEY: modified_base
<222> LOCATION: (12)..(12)
<223> OTHER INFORMATION: LNA

<400> SEQUENCE: 3
ccattagcag ctcacaa                                                     17

<210> SEQ ID NO 4
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 4
gctgaatcta taaaagctaa attag                                            25
```

```
<210> SEQ ID NO 5
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 5
cctctttcag caaatactt                                              19

<210> SEQ ID NO 6
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 6
tagttggtcc attagcagcc tcaca                                       25

<210> SEQ ID NO 7
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 7
gcggagtata tttagatgtt g                                           21

<210> SEQ ID NO 8
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 8
acggtctagt ccaataga                                               18

<210> SEQ ID NO 9
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 9
atgcttccag gtattcact                                              19

<210> SEQ ID NO 10
<211> LENGTH: 26
<212> TYPE: DNA
<213> ORGANISM: Artificial Sequence
<220> FEATURE:
<223> OTHER INFORMATION: synthetic oligonucleotide

<400> SEQUENCE: 10
ttgtatggat aggtggagaa gtcagt                                      26

<210> SEQ ID NO 11
<211> LENGTH: 31
<212> TYPE: DNA
<213> ORGANISM: Artificial Sequence
<220> FEATURE:
<223> OTHER INFORMATION: synthetic oligonucleotide
```

```
<400> SEQUENCE: 11
aatattatat tctgcattaa tatcagccca t                                31

<210> SEQ ID NO 12
<211> LENGTH: 22
<212> TYPE: DNA
<213> ORGANISM: Artificial Sequence
<220> FEATURE:
<223> OTHER INFORMATION: synthetic oligonucleotide
<220> FEATURE:
<221> NAME/KEY: modified_base
<222> LOCATION: (1)..(1)
<223> OTHER INFORMATION: FAM
<220> FEATURE:
<221> NAME/KEY: modified_base
<222> LOCATION: (22)..(22)
<223> OTHER INFORMATION: NFQ-MGB

<400> SEQUENCE: 12
atattgctct tgaatacata aa                                          22

<210> SEQ ID NO 13
<211> LENGTH: 23
<212> TYPE: DNA
<213> ORGANISM: Artificial Sequence
<220> FEATURE:
<223> OTHER INFORMATION: synthetic oligonucleotide
<220> FEATURE:
<221> NAME/KEY: modified_base
<222> LOCATION: (1)..(1)
<223> OTHER INFORMATION: FAM
<220> FEATURE:
<221> NAME/KEY: modified_base
<222> LOCATION: (23)..(23)
<223> OTHER INFORMATION: NFQ-MGB

<400> SEQUENCE: 13
tattgttctt gaatacataa aac                                         23

<210> SEQ ID NO 14
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 14
ggtggtatgt atttagatgt tga                                         23

<210> SEQ ID NO 15
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 15
tccactgtta ctgaactagg                                             20

<210> SEQ ID NO 16
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 16
ccaggaatac aaccagact                                              19
```

```
<210> SEQ ID NO 17
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 17
gaaacaggat ggacaccagg tt                                              22

<210> SEQ ID NO 18
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 18
aagaggatgg acgccaggtt                                                 20

<210> SEQ ID NO 19
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 19
acggtctaac agttttgtgc ca                                              22

<210> SEQ ID NO 20
<211> LENGTH: 27
<212> TYPE: DNA
<213> ORGANISM: Artificial Sequence
<220> FEATURE:
<223> OTHER INFORMATION: synthetic oligonucleotide

<400> SEQUENCE: 20
ctgcccttca taatgatctc ttatacg                                         27

<210> SEQ ID NO 21
<211> LENGTH: 17
<212> TYPE: DNA
<213> ORGANISM: Artificial Sequence
<220> FEATURE:
<223> OTHER INFORMATION: synthetic oligonucleotide
<220> FEATURE:
<221> NAME/KEY: modified_base
<222> LOCATION: (1)..(1)
<223> OTHER INFORMATION: FAM
<220> FEATURE:
<221> NAME/KEY: modified_base
<222> LOCATION: (17)..(17)
<223> OTHER INFORMATION: NFQ-MGB

<400> SEQUENCE: 21
aagaagctta gaaaatg                                                    17

<210> SEQ ID NO 22
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 22
```

-continued

```
gcatctgttg taagtagtct tg                                           22

<210> SEQ ID NO 23
<211> LENGTH: 28
<212> TYPE: DNA
<213> ORGANISM: Artificial Sequence
<220> FEATURE:
<223> OTHER INFORMATION: synthetic oligonucleotide

<400> SEQUENCE: 23
aggtgttaat ttattactcc aatcatta                                     28

<210> SEQ ID NO 24
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 24
aatttgcttt accccaagag tcccc                                        25

<210> SEQ ID NO 25
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 25
aatttgcttt accccaagag tcccc                                        25

<210> SEQ ID NO 26
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 26
ggtgccatta attttaaatc ttta                                         24

<210> SEQ ID NO 27
<211> LENGTH: 27
<212> TYPE: DNA
<213> ORGANISM: Artificial Sequence
<220> FEATURE:
<223> OTHER INFORMATION: synthetic oligonucleotide

<400> SEQUENCE: 27
agtgctcatc tgtgaaataa tatccca                                      27

<210> SEQ ID NO 28
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 28
gcacaaagga tattgctcta                                              20

<210> SEQ ID NO 29
<211> LENGTH: 18
<212> TYPE: DNA
<213> ORGANISM: Artificial Sequence
```

```
<220> FEATURE:
<223> OTHER INFORMATION: synthetic oligonucleotide

<400> SEQUENCE: 29
cctcatggtc ttcagaac                                              18

<210> SEQ ID NO 30
<211> LENGTH: 26
<212> TYPE: DNA
<213> ORGANISM: Artificial Sequence
<220> FEATURE:
<223> OTHER INFORMATION: synthetic oligonucleotide

<400> SEQUENCE: 30
tggcatttat tttggtgtgt tttttg                                     26
```

COMPOSITION AND KIT FOR DETECTION AND ANALYSIS OF STRAINS OF *CLOSTRIDIUM DIFFICILE* AND METHOD OF DETECTING STRAINS OF *CLOSTRIDIUM DIFFICILE* BY USING THE SAME

CROSS-REFERENCE TO RELATED APPLICATIONS

This application claims the benefit of Korean Patent Application No. 10-2012-0061671, filed on Jun. 8, 2012, in the Korean Intellectual Property Office, the disclosure of which is incorporated herein in its entirety by reference.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 6,934 Byte ASCII (Text) file named "711365_ST25.TXT," created on Jan. 30, 2013.

BACKGROUND

1. Field

The present disclosure relates to compositions and kits including primer sets for detecting strains of *Clostridium difficile* or virulent strains of *Clostridium difficile* and methods of detecting strains of *Clostridium difficile* in a sample by using the compositions or kits.

2. Description of the Related Art

*Clostridium difficile* is a species of Gram-positive bacteria of the genus Clostridia, which are anaerobic, spore-forming bacteria.

*Clostridium difficile* is the most serious cause of antibiotic-associated diarrhea and can lead to pseudomembranous colitis and a severe infection of the colon, often resulting in eradication of the normal gut flora by antibiotics. The *Clostridium difficile*, which naturally reside in the body, become overgrown. The overgrowth is harmful because the bacterium releases toxins that can cause bloating, constipation, and diarrhea with abdominal pain. Latent symptoms often mimic some flu-like symptoms. Discontinuation of causative antibiotic treatment is often curative.

Infections by *Clostridium difficile* can range in severity from asymptomatic to severe and life-threatening, especially among the elderly. People most often get infected in hospitals, nursing homes, or institutions, although infection by *Clostridium difficile* in the community in outpatient settings is increasing. The rate of *Clostridium difficile* acquisition is estimated to be 13% in patients with hospital stays of up to 2 weeks and 50% in those with hospital stays longer than 4 weeks. Frequency and severity of *Clostridium difficile* colitis remains high and seems to be associated with increased death rates. Early intervention and aggressive management are key factors to recovery.

Virulence factors of *Clostridium difficile* are toxin A, toxin B, a binary toxin, and a hypervirulent toxin. The toxin A, an enterotoxin, is encoded by tcdA genes. The toxin B, an enterotoxin, is encoded by tcdB genes. The binary toxin is encoded by cdtA and cdtB genes, and its virulence mechanism has not been identified yet. The hypervirulent toxin is related to virulent NAP1/BI/027 strains and is caused by Δ117 tcdC SNP (single nucleotide polymorphism). The emergence of a new, highly toxic strain of *Clostridium difficile*, resistant to fluoroquinolone antibiotics, such as Cipro (ciprofloxacin) and Levaquin (levofloxacin), said to be causing geographically dispersed outbreaks in North America was reported in 2005.

When these virulence genes are used for molecular diagnosis, there is a possibility of error occurrence due to variation of the genes and a likelihood of a false positive determination because of the variation. Thus, there is a need to detect *Clostridium difficile* by using a gene encoding a protein that is commonly expressed in various strains of *Clostridium difficile*.

In addition, virulent *Clostridium difficile* induces contagious infection through its spores, and patients with the virulent strain need to be isolated. Therefore, there is a need to perform accurate and rapid diagnosis by specifically detecting virulent strains of *Clostridium difficile* within a short period of time.

Thus, there is a need to develop a method of primarily detecting *Clostridium difficile* by using a gene with little variation that is commonly expressed in various strains of *Clostridium difficile*, of detecting virulent *Clostridium difficile* strains from the detected *Clostridium difficile* strains with high accuracy and sensitivity within a short period of time, and of diagnosing them.

SUMMARY

The invention provides compositions, kits, and methods for detecting a strain of *Clostridium difficile*.

The inventive composition and kits comprise at least one primer set selected from a primer set comprising at least 10 consecutive nucleotides selected from the nucleotide sequence of SEQ ID NO: 1 and at least 10 consecutive nucleotides selected from the nucleotide sequence of SEQ ID NO: 2; and a primer set comprising at least 10 consecutive nucleotides selected from the nucleotide sequence of SEQ ID NO: 4 and at least 10 consecutive nucleotides selected from the nucleotide sequence of SEQ ID NO: 5.

The method of detecting a strain of *Clostridium difficile* in a sample comprises (a) hybridizing a nucleic acid sequence obtained from the sample with at least one primer set selected from a primer set comprising at least 10 consecutive nucleotides selected from the nucleotide sequence of SEQ ID NO: 1 and at least 10 consecutive nucleotides selected from the nucleotide sequence of SEQ ID NO: 2; and a primer set comprising at least 10 consecutive nucleotides selected from the nucleotide sequence of SEQ ID NO: 4 and at least 10 consecutive nucleotides selected from the nucleotide sequence of SEQ ID NO: 5; (b) amplifying a target nucleic acid sequence; and (c) detecting the amplified target nucleic acid sequence.

BRIEF DESCRIPTION OF THE DRAWINGS

These and/or other aspects will become apparent and more readily appreciated from the following description of the embodiments, taken in conjunction with the accompanying drawings in which:

FIGS. 1(a)-(b) have response unit (RU) on the y-axis and cycle number on the x-axis.

FIGS. 2(a)-(b) have response unit (RU) on the y-axis and cycle number on the x-axis.

FIGS. 4(a)-(b) have response unit (RU) on the y-axis and cycle number on the x-axis.

FIGS. 6(a)-(b) show response unit (RU) on the y-axis and cycle number on the x-axis.

FIGS. 7(a)-(b) are images showing results of detecting a strain of Clostridium difficile by using primers having sequences of SEQ ID NOS: 22 to 24 to detect a target cdtA gene (see (a)) and by using primers having sequences of SEQ ID NOS: 25 to 27 to detect a target cdtB gene (see (b)), according to exemplary embodiments.

FIGS. 8(a)-(b) have response unit (RU) on the y-axis and cycle number on the x-axis.

DETAILED DESCRIPTION

Figure 1A:
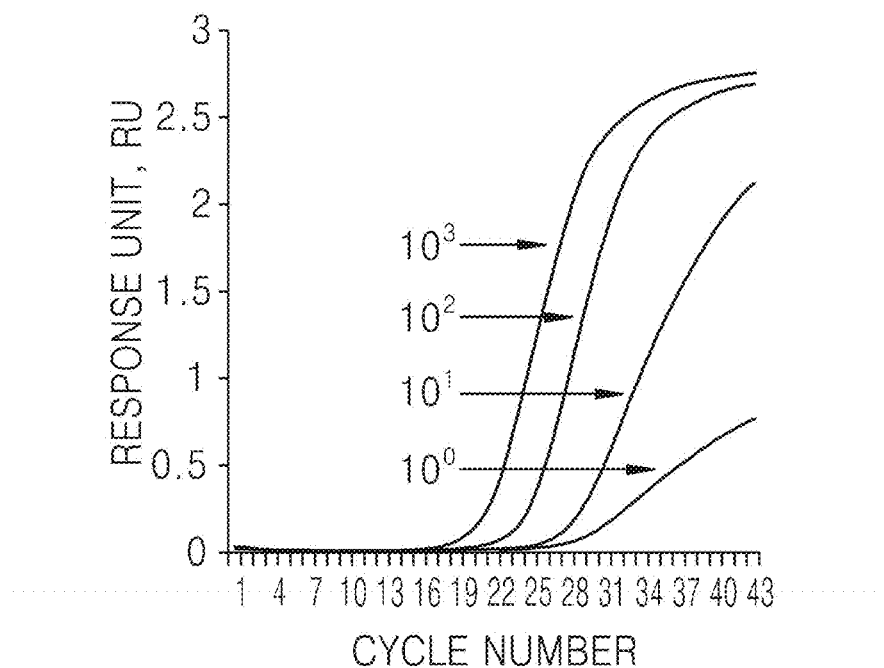
FIGS. 1(a)-(d) are graphs and images showing results of detecting a strain of *Clostridium difficile* by using primers having sequences of SEQ ID NOS: 1 to 3 to detect a gluD gene (see (a) and (c)) and by using primers having sequences of SEQ ID NOS: 4 to 6 to detect a gluD gene (see (b) and (d)), according to exemplary embodiments.
Figure 1B:
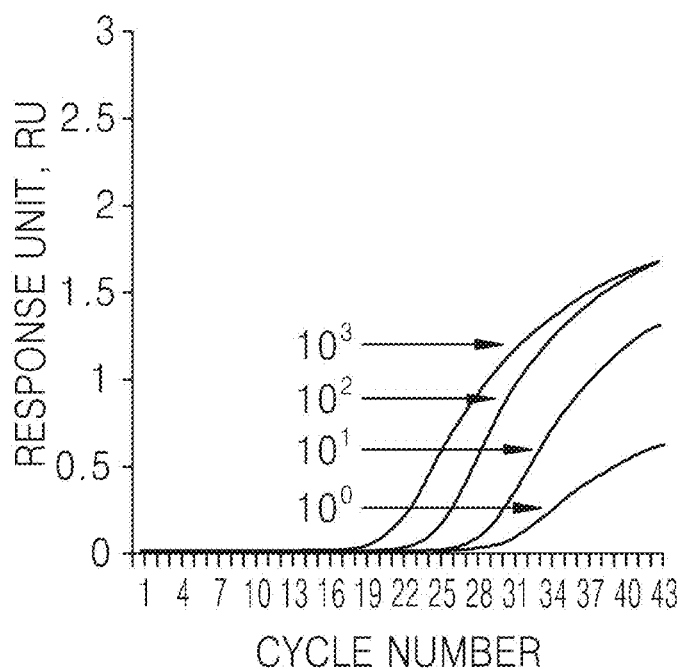
Figure 1C:
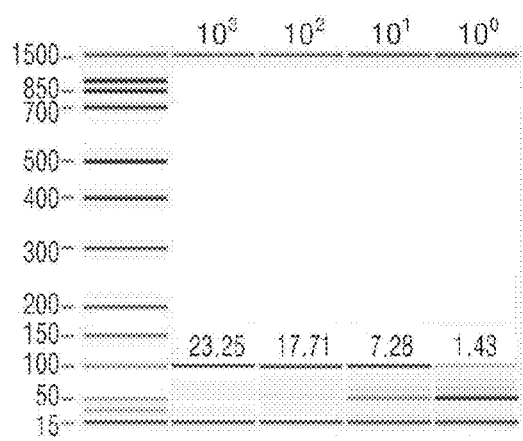
Figure 1D:
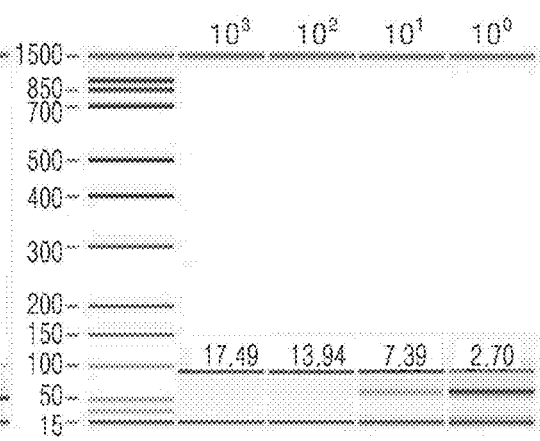

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items.

According to an embodiment of the present invention, a composition, system, or kit for detecting a strain of Clostridium difficile is provided, which includes at least one primer set selected from a primer set including at least 10 consecutive nucleotides selected from the nucleotide sequence of SEQ ID NO: 1 and at least 10 consecutive nucleotides selected from the nucleotide sequence of SEQ ID NO: 2; and a primer set including at least 10 consecutive nucleotides selected from the nucleotide sequence of SEQ ID NO: 4 and at least 10 consecutive nucleotides selected from the nucleotide sequence of SEQ ID NO: 5. The composition or kit may further include a probe including the nucleotide sequence of SEQ ID NO: 3 or 6.

A target nucleic acid having the sequences of SEQ ID NOs: 1 to 6 may be a gluD (glutamate dehydrogenase; GDH) gene. A gluD protein encoded by a gluD gene, which is a metabolic enzyme that is expressed in Clostridium difficile, is expressed in both an avirulent strain of Clostridium difficile and a virulent strain of Clostridium difficile. Thus, various strains of Clostridium difficile may be detected with high sensitivity by detecting a gluD gene regardless of whether Clostridium difficile is virulent or avirulent. In addition, by detecting the gluD gene, it may be likely to reduce the possibility of error occurrence due to the gene variation of a pathogenic gene or the likelihood of a false positive determination. Moreover, a size of a PCR product that is amplified by the primer set is in a range of 40 bp to 150 bp, which may enable specific detection of Clostridium difficile within a short period of time.

The composition or kit may further include a primer set including at least 10 consecutive nucleotides selected from the nucleic sequence of SEQ ID NO: 14 and at least 10 consecutive nucleotides selected from the nucleotide sequence of SEQ ID NO: 15. In addition, the composition may further include a probe including the nucleotide sequence of SEQ ID NO: 16.

A target nucleic acid having the sequences of SEQ ID NOS: 14 to 16 may be a Clostridium difficile toxin B (tcdB) gene. A tcdB protein that is encoded by the tcdB gene induces the virulence of Clostridium difficile. Although the tcdB gene has little conserved regions among various strains of Clostridium difficile, a virulent Clostridium difficile strain may be detected with high sensitivity by using a primer set designed to have an improved sensitivity with respect to the tcdB gene. Moreover, a size of a PCR product that is amplified by the primer set is in a range of 40 bp to 100 bp, which may enable specific detection of a virulent Clostridium difficile strain within a short period of time.

The composition or kit may further include a primer set including: at least 10 consecutive nucleotides selected from the nucleic sequence of SEQ ID NO: 28 and at least 10 consecutive nucleotides selected from the nucleotide sequence of SEQ ID NO: 29. In addition, the composition may further include a probe including the nucleotide sequence of SEQ ID NO: 30.

A target nucleic acid having the sequences of SEQ ID NOS: 28 to 30 may be a tcdC gene having Δ117 single nucleotide polymorphism (SNP). SNP at position 117 of the tcdC gene is a virulent gene that is confirmed in a hypervirulent Clostridium difficile strain. To detect the tcdC gene containing Δ117 SNP, an allele-specific primer set capable of detecting without using an additional primer or probe may be used, whereby a hypervirulent Clostridium difficile strain may be detected with high sensitivity. Moreover, a size of a PCR product that is amplified by the primer set is in a range of 40 bp to 100 bp, which may enable specific detection of the hypervirulent *Clostridium difficile* strain within a short period of time. The sequences of SEQ ID NOs: 28 and 29 are primers for amplification to detect an allele-specific region, and the sequence of SEQ ID NO: 30 is an allele-specific probe.

The composition or kit may further include at least one primer set selected from a primer set including at least 10 consecutive nucleotides selected from the nucleotide sequence of SEQ ID NO: 7 and at least 10 consecutive nucleotides selected from the nucleotide sequence of SEQ ID NO: 8; a primer set including at least 10 consecutive nucleotides selected from the nucleotide sequence of SEQ ID NO: 22 and at least 10 consecutive nucleotides selected from the nucleotide sequence of SEQ ID NO: 23; and a primer set including at least 10 consecutive nucleotides selected from the nucleotide sequence of SEQ ID NO: 25 and at least 10 consecutive nucleotides selected from the nucleotide sequence of SEQ ID NO: 26. In addition, the composition may further include a probe including at least one nucleotide sequence selected from the group consisting of sequences of SEQ ID NOS: 9, 24, and 27.

A target nucleic acid having the sequences of SEQ ID NOS: 7 to 9 may be a *Clostridium difficile* toxin A (tcdA) gene. A tcdA protein that is encoded by the tcdA gene induces the virulence of *Clostridium difficile*. A virulent *Clostridium difficile* strain may be detected with high sensitivity using a primer set designed to have an improved sensitivity with respect to the tcdA gene.

A target nucleic acid having the sequences of SEQ ID NOS: 22 to 24 may be a cdtA gene encoding a binary toxin. *Clostridium difficile* with binary virulence may be detected with high sensitivity using a primer set that is uniquely designed for the cdtA gene.

A target nucleic acid having the sequences of SEQ ID NOS: 25 to 27 may be a cdtB gene. *Clostridium difficile* with binary virulence may be detected with high sensitivity using a primer set that is uniquely designed for the cdtB gene. Moreover, a size of a PCR product that is amplified by the primer sets is in a range of 40 bp to 100 bp, which may enable specific detection of a virulent *Clostridium difficile* strain within a short period of time.

The composition, system, or kit may include any one or more (e.g., two or more, or three or more) primer sets and/or probes described above, each primer set and/or probe being targeted to different genes, different regions of the same gene, or both.

In addition, any one or more probes used in the composition or kit may be labeled with a fluorescence resonance energy transfer (FRET) pair. Also, for example, the probe may be labeled at the 5'-terminal thereof with at least one fluorescent marker selected from the group consisting of FAM, VIC, TET, JOE, HEX, CY3, CY5, ROX, RED610, TEXAS RED, RED670, and NED, or the probe may be labeled at the 3'-terminal thereof with at least one fluorescent quencher selected from the group consisting of 6-TAMRA, BHQ-1,2,3, and a molecular groove binding non-fluorescence quencher (MGBNFQ).

In detecting a strain of *Clostridium difficile*, the primer set may suppress self-dimerization by using its uniquely designed sequence, reduce or eliminate cross-reactivity of the primer set so that detection efficiency and sensitivity is improved, and/or allow detection of a strain of *Clostridium difficile* on the basis of a combination of genes to improve specificity. In addition, the size of an amplicon produced for each gene may be equal to or less than 100 bp, and, thus, a target may be specifically amplified within a short period of time. The at least one combination of a plurality of genes may be detected in real time simultaneously in at least one space, whereby a detection time may be minimized.

The term "nucleotide sequence" as used herein refers to a double-stranded DNA or cDNA, or a single-stranded DNA or RNA. Unless otherwise indicated herein, the nucleotide sequence may be intended to include a nucleotide analogue. The nucleotide sequence may be synthesized and produced using an appropriate method known in the art (e.g., chemical synthesis). In addition, a commercially available nucleotide sequence may be used.

In some embodiments, the term "nucleotide sequence" as used herein may be intended to indicate the term "nucleic acid sequence," "primer," "oligonucleotide," or "polynucleotide."

A nucleotide may be synthesized and produced using an appropriate method known in the art (e.g., chemical synthesis). Also, a commercially available nucleotide may be used.

The term "primer" as used herein refers to a single-stranded oligonucleotide capable of acting as a point of initiation of template-dependent DNA synthesis under appropriate conditions (e.g., in the presence of four different nucleoside triphosphates and an enzyme for polymerization) in a suitable buffer and at a suitable temperature.

An appropriate length of a primer may vary according to temperature and use of the primer, but typically ranges from 15 to 35 nucleotides (e.g., 16, 17, 18, 19, 20, 21, 22, 23, 24, 25, 26, 27, 28, 29, 30, 31, 32, 33, or 34 nucleotides). A relatively short primer may generally require a relatively low temperature to form a sufficiently stable hybrid complex with a template. The terms "forward primer" and "reverse primer" as used herein refers to primers that are respectively linked to the 3' terminal and the 5' terminal of a certain region of a template that is amplified by a polymerase chain reaction (PCR).

The primer may be hybridized with, or annealed to, a region of a template nucleic acid to form a double-stranded structure. Conditions suitable for nucleic acid hybridization to form such a double-stranded structure are well known in the art.

The term "probe" as used herein refers to a linear oligomer of natural or modified monomers or linkages, including deoxyribonucleotides and/or ribonucleotides, which is capable of hybridizing with a target polynucleotide sequence. For example, the probe may be single-stranded in order to improve hybridization efficiency. The probe may be a sequence that is completely complementary to a polynucleotide sequence as a template. In one embodiment, however, the probe may be a substantially complementary sequence as long as it does not interfere with specific hybridization.

The term "substantially complementary sequence" as used herein refers to a sequence capable of hybridizing with a polynucleotide as a template under stringent conditions known in the art. The stringent conditions may be determined by adjusting a temperature, an ionic strength (buffer concentration), the presence of a compound such as an organic solvent, or the like, and may vary according to a sequence to be hybridized. For example, the stringent conditions may be the following conditions: a) at 50° C. and washing with 0.015 M sodium chloride/0.0015 M sodium citrate/0.1% sodium dodecyl sulfate; b) hybridizing in a hybridization buffer (including 50% formamide, 2×SSC and 10% dextran sulfate) at 55° C. and then washing with EDTA-containing 0.1×SSC at 55° C.

The term "target DNA," "target RNA," "target nucleic acid," or "target nucleic acid sequence" as used herein refers to a nucleic acid that is targeted by DNA amplification. A target nucleic acid sequence may serve as a template for amplification in a PCR or a reverse transcription (RT)-PCR. Target nucleic acid sequences include natural molecules and synthetic molecules. For example, target nucleic acids may be a genomic DNA or a genomic RNA.

The composition or kit may be used to amplify a target nucleic acid. The amplifying method may be any suitable method for nucleic acid amplification which is known in the art. The amplification may be, for example, DNA amplification or RNA amplification. The amplifying method may be an amplifying method requiring thermal cycling or an isothermal amplifying method. The amplifying method may include a PCR, a nucleic acid sequence-based amplification (NASBA), a ligase chain reaction (LCR), a strand displacement amplification (SDA), a rolling circle amplification (RCA), and the like. Also, the amplifying method may include an RNA amplification method. Examples of the amplifying method include RT and RT-PCR. The term "amplifying" as used herein may be intended to mean a process of increasing the number of copies of a target nucleic acid sequence or sequence complementary thereto. The term "PCR (polymerase chain reaction)" as used herein refers to a method of amplifying a target nucleic acid from a primer pair that is specifically binding to the target nucleic acid by using a polymerase.

In addition, the composition or kit may further include a known material required for the amplification of a target nucleic acid. For example, the composition may further include a nucleic acid polymerase, a buffer required for the activity thereof, a cofactor, and/or a substrate. The nucleic acid polymerase may be a DNA polymerase, an RNA polymerase, a reverse transcriptase, or a combination thereof. The term "reverse transcription" as used herein refers to synthesis of a DNA strand from an RNA template, in which the DNA strand is complementary to a sequence of the RNA. The nucleic acid polymerase may have strand displacement activity. For example, the nucleic acid polymerase may be at least one reverse transcriptase derived from retrovirus, for example, HIV, MMLV, and AMV. The nucleic acid polymerase may not have 3'->5' exonuclease activity. The composition may include a material required for RT or PCR amplification.

According to another embodiment of the present invention, a method of detecting a strain of *Clostridium difficile* in a sample in real time is provided, which method includes: hybridizing a nucleic acid sequence from the sample with at least one primer set selected from a primer set including at least 10 consecutive nucleotides selected from the nucleotide sequence of SEQ ID NO: 1 and at least 10 consecutive nucleotides selected from the nucleotide sequence of SEQ ID NO: 2; and a primer set including at least 10 consecutive nucleotides selected from the nucleotide sequence of SEQ ID NO: 4 and at least 10 consecutive nucleotides selected from the nucleotide sequence of SEQ ID NO: 5; amplifying a target nucleic acid sequence; and detecting the amplified target nucleic acid sequence.

In addition, the method may further include hybridizing the amplified target nucleic acid sequence with a probe including the nucleotide sequence of SEQ ID NO: 3 or 6.

The method may further include hybridizing the nucleic acid sequence obtained from the sample with a primer set including at least 10 consecutive nucleotides selected from the nucleotide sequence of SEQ ID NO: 14 and at least 10 consecutive nucleotides selected from the nucleotide sequence of SEQ ID NO: 15. In addition, the method may further include hybridizing the amplified target nucleic acid sequence with a probe including the nucleotide sequence of SEQ ID NO: 16.

The method may further include hybridizing the nucleic acid sequence obtained from the sample with a primer set including at least 10 consecutive nucleotides selected from the nucleotide sequence of SEQ ID NO: 28 and at least 10 consecutive nucleotides selected from the nucleotide sequence of SEQ ID NO: 29. In addition, the method may further include hybridizing the amplified target nucleic acid sequence with a probe including the nucleotide sequence of SEQ ID NO: 30.

The method may further include hybridizing the nucleic acid sample obtained from the sample with at least one primer set selected from a primer set including at least 10 consecutive nucleotides selected from the nucleotide sequence of SEQ ID NO: 7 and at least 10 consecutive nucleotides selected from the nucleotide sequence of SEQ ID NO: 8; a primer set including at least 10 consecutive nucleotides selected from the nucleotide sequence of SEQ ID NO: 22 and at least 10 consecutive nucleotides selected from the nucleotide sequence of SEQ ID NO: 23; and a primer set including at least 10 consecutive nucleotides selected from the nucleotide sequence of SEQ ID NO: 25 and at least 10 consecutive nucleotides selected from the nucleotide sequence of SEQ ID NO: 26. In addition, the method may further include hybridizing the amplified nucleic acid sequence with a probe including at least one nucleotide sequence selected from the group consisting of sequences of SEQ ID NOS: 9, 24, and 27.

The nucleic acid sequence obtained from the sample may be an extract genomic DNA or purified extract genomic DNA from an excrement sample, a sample collected with a cotton swab, body fluid, or a tissue section.

In the hybridizing process, the term "hybridizing" used herein may be also referred to as the term "annealing." The hybridization refers to a process in which a nucleic acid and another nucleic acid form a duplex, triplex, or multiplex structure through base-pairing interaction therebetween. The base-pairing interaction may be base-specific base pairing by Watson/Crick and Hoogsteen-type hydrogen bonding. In addition, base-stacking and hydrophobic interaction may contribute to the stability of the duplex.

The method includes amplifying a sequence of the target nucleic acid.

The target nucleic acid sequence refers to a nucleic acid that is targeted by DNA amplification. The target nucleic acid sequence may serve as a template for amplification in a PCR or a RT-PCR. The target nucleic acid sequence may include a natural molecule and a synthetic molecule. The target nucleic acid may be, for example, a genomic DNA or a genomic RNA.

The size of the amplified target nucleic acid sequence may be in a range of 40 bp to 100 bp, and thus, a time taken for amplification and detection is minimized, whereby strains of *Clostridium difficile* may be rapidly detected.

The amplifying process may be performed using a known method used for the amplification of a nucleic acid. The amplification may be, for example, DNA amplification or RNA amplification. The amplifying method may be an amplifying method requiring thermal cycling or an isothermal amplifying method. The amplifying method may include a PCR, an NASBA, an LCR, an SDA, an RCA, and the like. Also, the amplifying method may include an RNA amplification method. Examples of the amplifying method include RT and RT-PCR. The term "amplifying" as used herein may be intended to mean a process of increasing the number of copies of a target nucleic acid sequence or sequence complementary thereto. The term "PCR" as used herein refers to a method of amplifying a target nucleic acid from a primer pair that is specifically binding to the target nucleic acid by using a polymerase. The PCR is well known in the art. For example, the PCR may be performed by using the following processes: 1) processing a sample to obtain an extract in order to isolate a target DNA molecule; 2) adding thereto an aqueous solution containing an enzyme, a buffer, dNTP, and an oligonucleotide primer; 3) thermally cycling the reaction mixture between two to three kinds of temperatures, for example, 90° C. to 96° C., 37° C. to 65° C., and 72° C.; and 4) detecting the amplified DNA. The PCR may be performed in a polypropylene tube, a 96-well plate, or a silicon-based micro PCR chip. In addition, the amplification may be multiplex PCR. The term "multiplex PCR" used herein refers to a reaction in which a plurality of primer sets are subjected to a PCR simultaneously in the same chamber.

The method includes detecting the amplified target nucleic acid sequence.

The detecting process indicates a process of detecting a signal generated from a detectable marker by using a detector. For example, the signal generated from a detectable marker may be selected from the group consisting of a magnetic signal, an electrical signal, a luminescent signal such as a fluorescent signal and a Raman signal, a scattering light signal, and a radioactive signal. In the detecting process, a signal generated from a detectable marker with which a target sequence is labeled may be detected. For example, in the detecting process, it may be detected whether or not a target nucleic acid is present by detecting a signal generated by FRET.

In the detecting process, nucleic acid sequences that are amplified in real time may be detected in real time. Therefore, a target nucleic acid sequence may be detected within a short period of time.

One or more embodiments of the present invention will now be described more fully with reference to the following examples. However, these examples are provided only for illustrative purposes and are not intended to limit the scope of the present invention.

EXAMPLE 1

This example describes the selection of primers and probe for the detection of *Clostridium difficile* and PCR evaluation.

When pathogenic genes are used for molecular diagnosis, there is a possibility of error occurrence due to variation of the genes and a likelihood of a false positive determination. Thus, there is a need to use in molecular diagnosis a gene that has little variation and is commonly expressed in various strains of *Clostridium difficile*.

gluD (glutamate dehydrogenase) is a protein that is commonly expressed in various strains of *Clostridium difficile* and has little variation, and thus, various strains of *Clostridium difficile* may be detected by gluD regardless of whether *Clostridium difficile* is avirulent or virulent.

Therefore, each of the two primer sets for detecting strains of *Clostridium difficile* by specifically amplifying a gluD gene encoding a gluD protein and a probe for real-time PCR detection were designed through an NCBI website and interactivity thereof was analyzed and verified.

The primer set and the probe were as follows:

```
                                         (SEQ ID NO: 1)
Forward primer: 5'-GCTGCATTAGAAAACTCTATAAC-3', (SEQ ID NO: 2)
Reverse primer: 5'-CAGCCTCTGGAGTAGTTG-3',
and (SEQ ID NO: 3)
Probe:          5'-CCATTAGCAGCTCACAA-3'
(The underlined nucleic acids denote
LNA).
```

Alternatively, the primer set and the probe were as follows:

```
Forward primer:
                                         (SEQ ID NO: 4)
5'-GCTGAATCTATAAAAGCTAAATTAG-3', Reverse primer:
                                         (SEQ ID NO: 5)
5'-CCTCTTTCAGCAAATACTTC-3',
and Probe:
                                         (SEQ ID NO: 6)
5'-TAGTTGGTCCATTAGCAGCCTCACA-3'.
```

The real-time PCR analysis results of *Clostridium difficile* are shown in FIG. 1.

The size of a gluD gene that was PCR-amplified by the primer set having the sequences of SEQ ID NOS: 1 and 2 was 97 bp, and the size of a gluD gene that was PCR-amplified by the primer set having the sequences of SEQ ID NOS: 4 and 5 was 85 bp. At least 1 copy of the gluD gene was detectable using the primer sets. Therefore, the strains of *Clostridium difficile* may be detected with high sensitivity within a short period of time.

EXAMPLE 2

This example describes the selection of primers and probe for the detection of toxin A of *Clostridium difficile* strain and PCR evaluation.

A virulent *Clostridium difficile* strain may be detected by toxin A that induces the virulence of *Clostridium difficile*.

A primer set for specifically amplifying tcdA, which is a gene of toxin A of *Clostridium difficile*, and a probe for real-time PCR detection were designed through an NCBI website and interactivity thereof was analyzed and verified. The designed primer set and probe for real-time PCR detection had an improved sensitivity.

The primer set and the probe were as follows:

```
Forward primer:
                                         (SEQ ID NO: 7)
5'-GCGGAGTATATTTAGATGTTG-3', Reverse primer:
                                         (SEQ ID NO: 8)
5'-ACGGTCTAGTCCAATAGA-3',
and Probe:
                                         (SEQ ID NO: 9)
5'-ATGCTTCCAGGTATTCACT-3'.
```

A reference-tcdA was amplified using the following primer set (see de Boer et al., *J Microbiol Methods*, 83: 59-65 (2010)):

```
Forward primer:
                                         (SEQ ID NO: 10)
5'-TTGTATGGATAGGTGGAGAAGTCAGT-3', Reverse primer:
                                         (SEQ ID NO: 11)
5'-AATATTATATTCTGCATTAATATCAGCCCAT-3',
```

-continued

```
Probe 1:
                                    (SEQ ID NO: 12)
5'-FAM-ATATTGCTCTTGAATACATAAA-NFQ-MGB-3',
and Probe 2:
                                    (SEQ ID NO: 13)
5'-FAM-TATTGTTCTTGAATACATAAAAC-NFQ-MGB-3'.
```

Figure 2A:
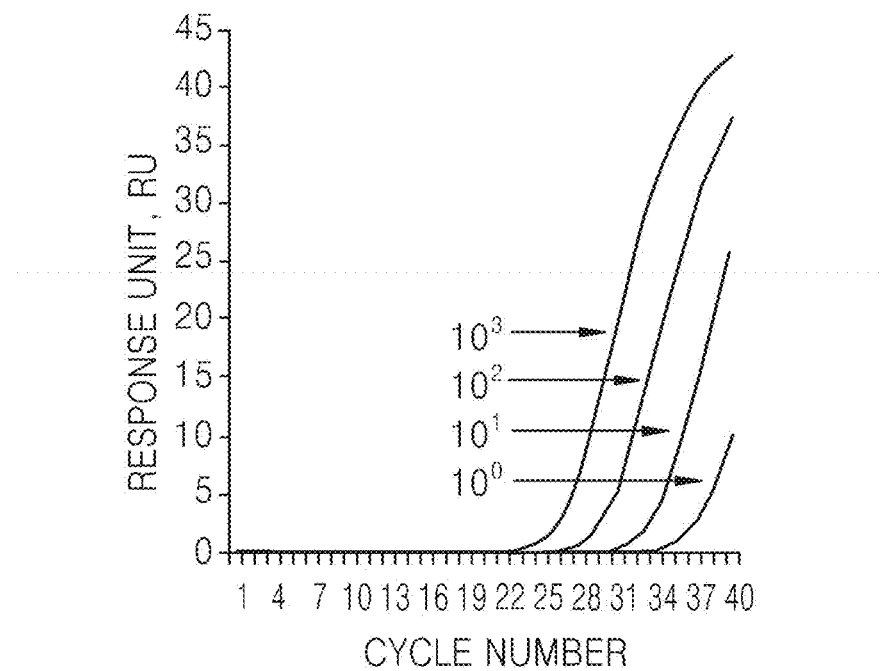
FIGS. 2(a)-(b) are graphs showing results of detecting a strain of *Clostridium difficile* by using primers having sequences of SEQ ID NOS: 7 to 9 to detect a target tcdA gene (see (a)) and by using primers having sequences of SEQ ID NOS: 10 and 11 to detect a reference-tcdA gene (see (b)) and a probe having the sequence of SEQ ID NO: 12 or 13, according to exemplary embodiments.
Figure 2B:
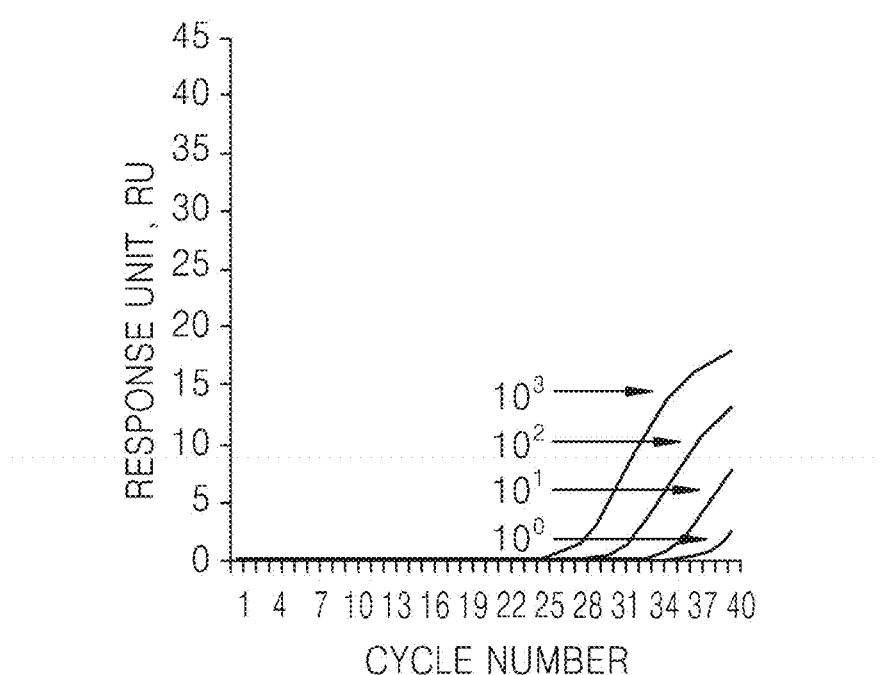
Figures 3A, 3B:
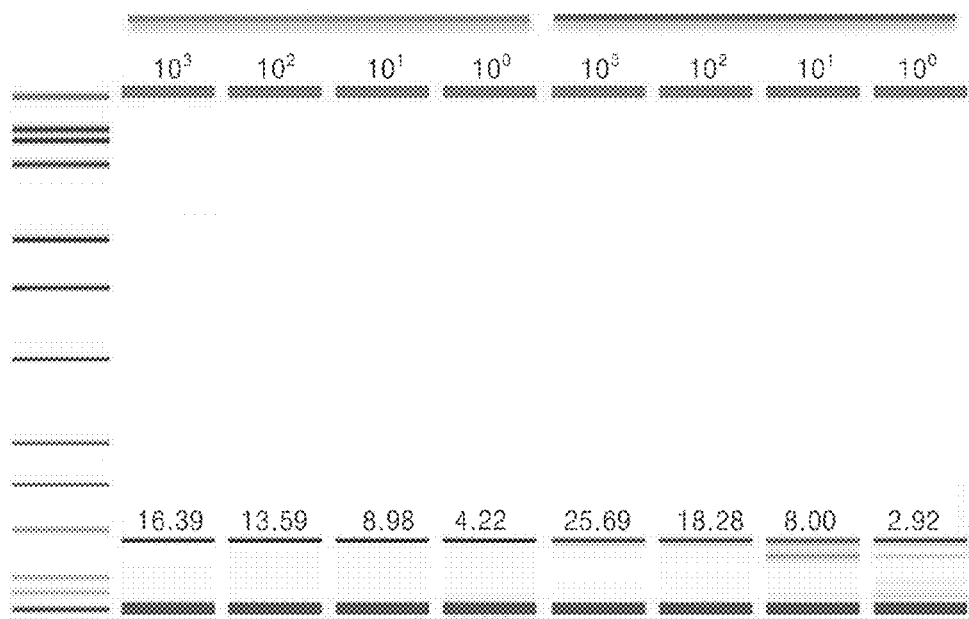
FIGS. 3(a)-(b) are images showing results of detecting a strain of Clostridium difficile by using primers having sequences of SEQ ID NOS: 7 to 9 to detect a target tcdA gene (see (a)) and by using primers having sequences of SEQ ID NOS: 10 and 11 to detect a reference-tcdA gene (see (b)) and a probe having the sequence of SEQ ID NO: 12 or 13, according to exemplary embodiments.

The real-time PCR analysis results of *Clostridium difficile* are shown in FIGS. 2 and 3.

The size of a PCR product that was amplified by the primer set having the sequences of SEQ ID NOS: 7 and 8 was 92 bp. In addition, at least one copy of the tcdA gene was detectable using the primer set having the sequences of SEQ ID NOS: 7 and 8 as compared to the reference-tcdA. Therefore, a *Clostridium difficile* strain with virulence by the tcdA is detectable with high sensitivity within a short period of time.

EXAMPLE 3

This example describes the selection of primers and probe for detecting toxin B of *Clostridium difficile* and PCR evaluation.

A virulent *Clostridium difficile* may be detected by toxin B that induces the virulence of *Clostridium difficile*.

A toxin B gene, tcdB, is conserved little among various strains of *Clostridium difficile*. A primer set for specifically amplifying the tcdB and a probe for real-time PCR detection were designed through an NCBI website and interactivity thereof was analyzed and verified.

The designed primer set and probe for real-time PCR detection had an improved sensitivity.

The primer set and probe were as follows:

```
Forward primer:
                                    (SEQ ID NO: 14)
5'-GGTGGTATGTATTTAGATGTTGA-3', Reverse primer:
                                    (SEQ ID NO: 15)
5'-TCCACTGTTACTGAACTAGG-3',
and Probe:
                                    (SEQ ID NO: 16)
5'-CCAGGAATACAACCAGACT-3'.
```

A reference-tcdB was amplified using the following primer set (see de Bour et al., *J Microbiol Methods*, 83: 59-65 (2010)):

```
Forward primer:
                                    (SEQ ID NO: 17)
5'-GAAACAGGATGGACACCAGGTT-3'
or (SEQ ID NO: 18)
5'-AAGAGGATGGACGCCAGGTT-3', Reverse primer:
                                    (SEQ ID NO: 19)
5'-ACGGTCTAACAGTTTTGTGCCA-3'
or (SEQ ID NO: 20)
5'-CTGCCCTTCATAATGATCTCTTATACG-3',
and
```

```
Probe:
                                    (SEQ ID NO: 21)
5'-FAM-AAGAAGCTTAGAAAATG-NFQ-MGB-3'.
```

Figure 4A:
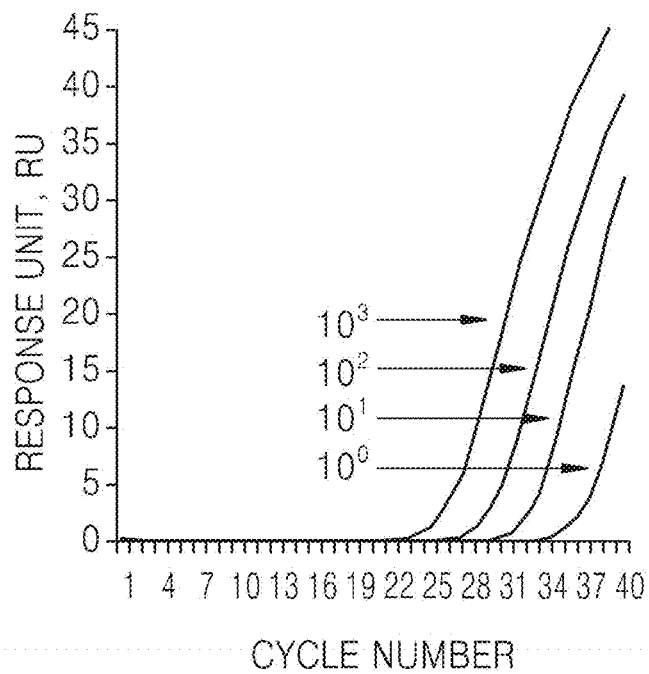
FIGS. 4(a)-(b) are graphs showing results of detecting a strain of Clostridium difficile by using primers having sequences of SEQ ID NOS: 14 to 16 to detect a target tcdB gene (see (a)) and by using a forward primer having the sequence of SEQ ID NO: 17 or 18 and a reverse primer having the sequence of SEQ ID NO: 19 or 20 to detect a reference-tcdB gene (see (b)), and a probe having the sequence of SEQ ID NO: 21, according to exemplary embodiments.
Figure 4B:
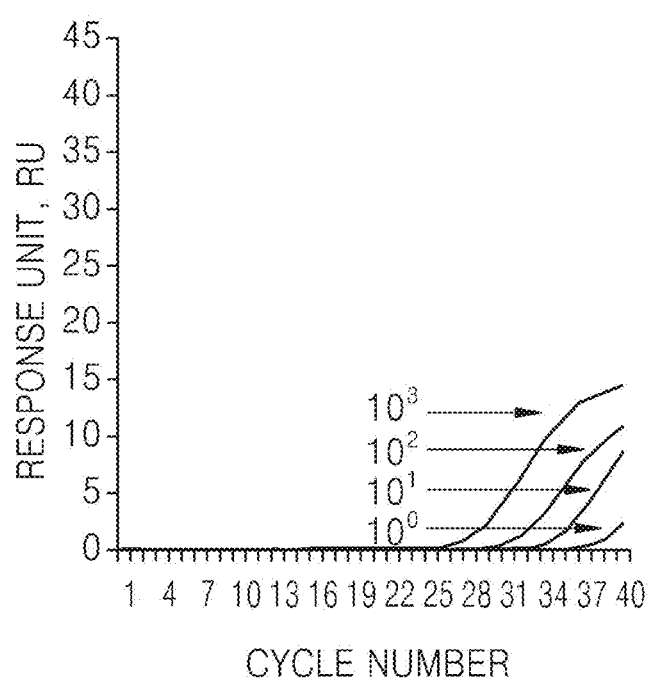
Figures 5A, 5B:
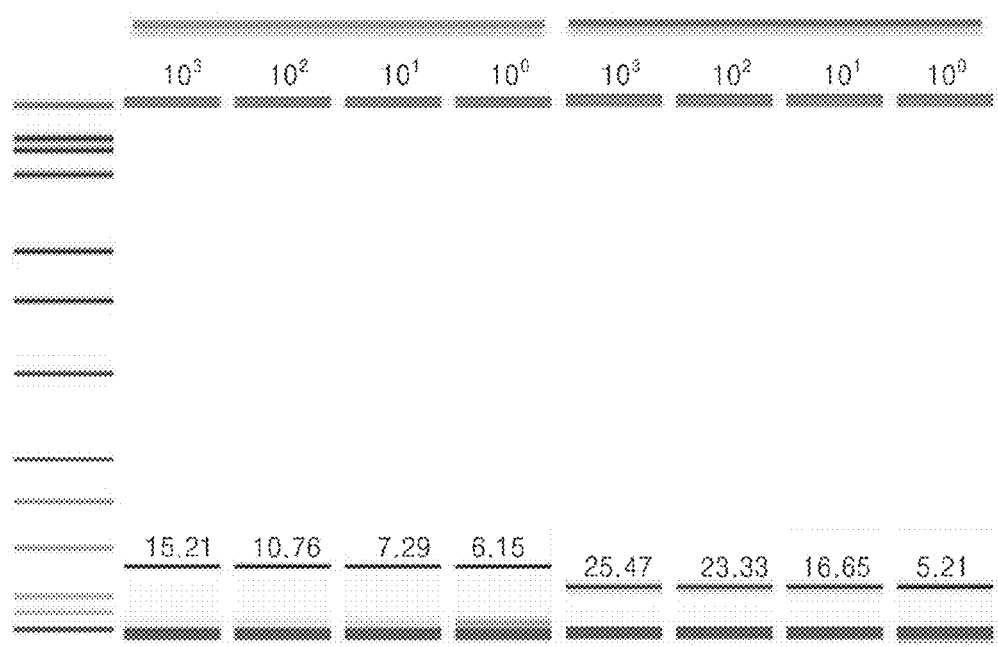
FIGS. 5(a)-(b) are images showing results of detecting a strain of Clostridium difficile by using primers having sequences of SEQ ID NOS: 14 to 16 to detect a target tcdB gene (see (a)) and by using a forward primer having the sequence of SEQ ID NO: 17 or 18 and a reverse primer having the sequence of SEQ ID NO: 19 or 20 to detect a reference-tcdB gene (see (b)), and a probe having the sequence of SEQ ID NO: 21, according to exemplary embodiments.

The real-time PCR analysis results of *Clostridium difficile* are shown in FIGS. 4 and 5.

The size of a PCR product that was amplified by the primer set having the sequences of SEQ ID NOS: 14 and 15 was 89 bp.

As compared to the reference-tcdB, at least one copy of the tcdB gene was detectable using the primer set having the sequences of SEQ ID NOS: 14 and 15. Therefore, a *Clostridium difficile* strain with virulence by the tcdB is detectable with high sensitivity within a short period of time.

EXAMPLE 4

This example describes the selection of primers and probe for detecting binary toxin of *Clostridium difficile* and PCR evaluation.

A virulent *Clostridium difficile* may be detected by a binary toxin that induces the virulence of *Clostridium difficile*.

A primer set for specifically amplifying cdtA and cdtB, which are binary toxin genes, and a probe for real-time PCR detection were designed through an NCBI website and interactivity thereof was analyzed and verified. The designed primer set and probe for real-time PCR detection had a unique design for each gene.

The sizes of cdtA and cdtB amplicons that were amplified by a PCR were 99 bp and 72 bp, respectively.

The primer set and probe for the cdtA gene were as follows:

```
Forward primer:
                                    (SEQ ID NO: 22)
5'-GCATCTGTTGTAAGTAGTCTTG-3', Reverse primer:
                                    (SEQ ID NO: 23)
5'-AGGTGTTAATTTATTACTCCAATCATTA-3',
and Probe:
                                    (SEQ ID NO: 24)
5'-AATTTGCTTTACCCCAAGAGTCCCC-3'.
```

The primer set and probe for the cdtB gene were as follows:

```
Forward primer:
                                    (SEQ ID NO: 25)
5'-ACTCCCAAACAATGGATTA-3', Reverse primer:
                                    (SEQ ID NO: 26)
5'-GGTGCCATTAATTTTAAATCTTTA-3',
and Probe:
                                    (SEQ ID NO: 27)
5'-AGTGCTCATCTGTGAAATAATATCCCA-3'.
```

Figure 6A:
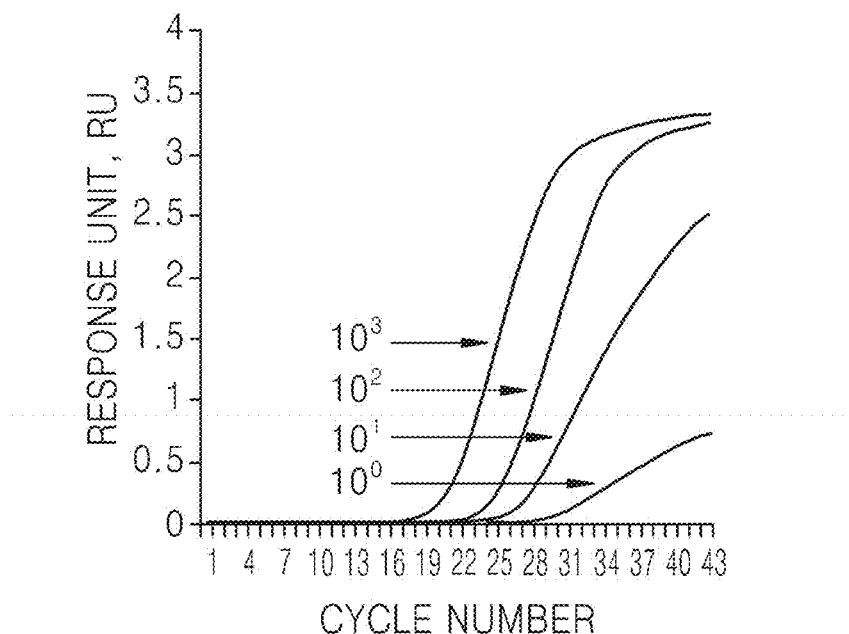
FIGS. 6(a)-(b) are graphs showing results of detecting a strain of Clostridium difficile by using primers having sequences of SEQ ID NOS: 22 to 24 to detect a target cdtA gene (see (a)) and by using primers having sequences of SEQ ID NOS: 25 to 27 to detect a target cdtB gene (see (b)), according to exemplary embodiments.
Figure 6B:
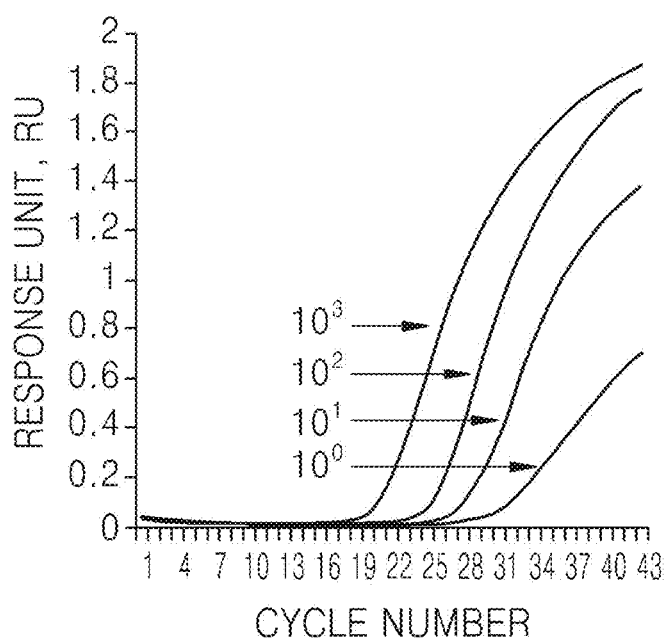

The real-time PCR analysis results of *Clostridium difficile* are shown in FIGS. 6 and 7.

The sizes of cdtA and cdtB products that were amplified by a PCR were 99 bp and 72 bp, respectively. At least one copy of each of the cdtA and cdtB genes was detected by the respective primer sets. Therefore, a *Clostridium difficile* strain with virulence by the binary toxin is detectable with high sensitivity.

EXAMPLE 5

This example describes the selection of primer and probe for detecting hypervirulent *Clostridium difficile* and PCR evaluation.

A tcdC gene having Δ117 SNP (single nucleotide polymorphism) of *Clostridium difficile* is present in hypervirulent strains that are resistant to fluoroquinolone antibiotics such as ciprofloxacin and levofloxacin. Thus, a hypervirulent *Clostridium difficile* may be detected by the tcdC gene having Δ117 SNP.

To detect *Clostridium difficile* that induces hypervirulence, a primer set for specifically amplifying a tcdC gene containing Δ117 SNP and a probe for real-time PCR detection were designed through an NCBI website and interactivity thereof was analyzed and verified.

The primer set and probe for real-time PCR detection were allele-specifically designed such that a hypervirulent *Clostridium difficile* was detectable using a primer set having allele-specific sequences without using additional primers and probe.

The primer set and probe were as follows:

```
Forward primer:
                                     (SEQ ID NO: 28)
5'-GCACAAAGGATATTGCTCTA-3', Reverse primer:
                                     (SEQ ID NO: 29)
5'-CCTCATGGTCTTCAGAAC-3',
and Probe:
                                     (SEQ ID NO: 30)
5'-TGGCATTTATTTTGGTGTGTTTTTTG-3'.
```

Figure 8A:
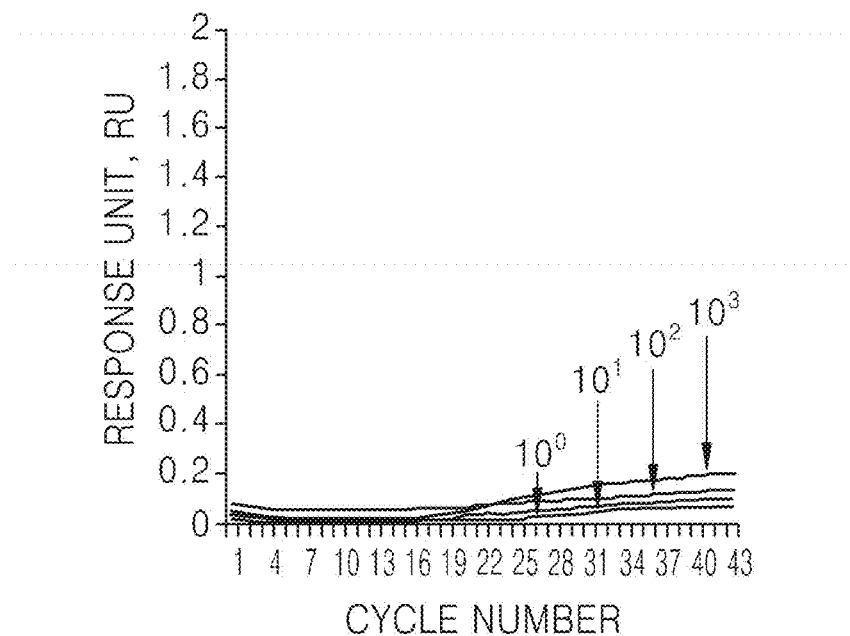
FIGS. 8(a)-(b) are graphs showing results of detecting a strain of Clostridium difficile by using primers for a wild-type tcdC gene (see (a)) and by using primers for a mutant tcdC gene containing Δ117 SNP that have sequences of SEQ ID NOS: 28 to 30 (see (b)), from which it was confirmed that the tcdC gene containing Δ117 SNP was specifically detectable.
Figure 8B:
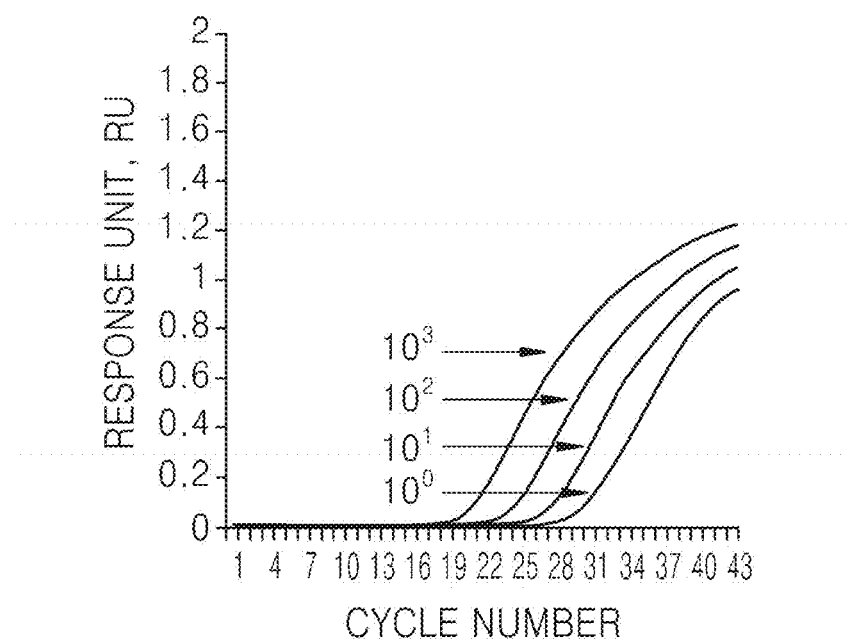
Figures 9A, 9B:
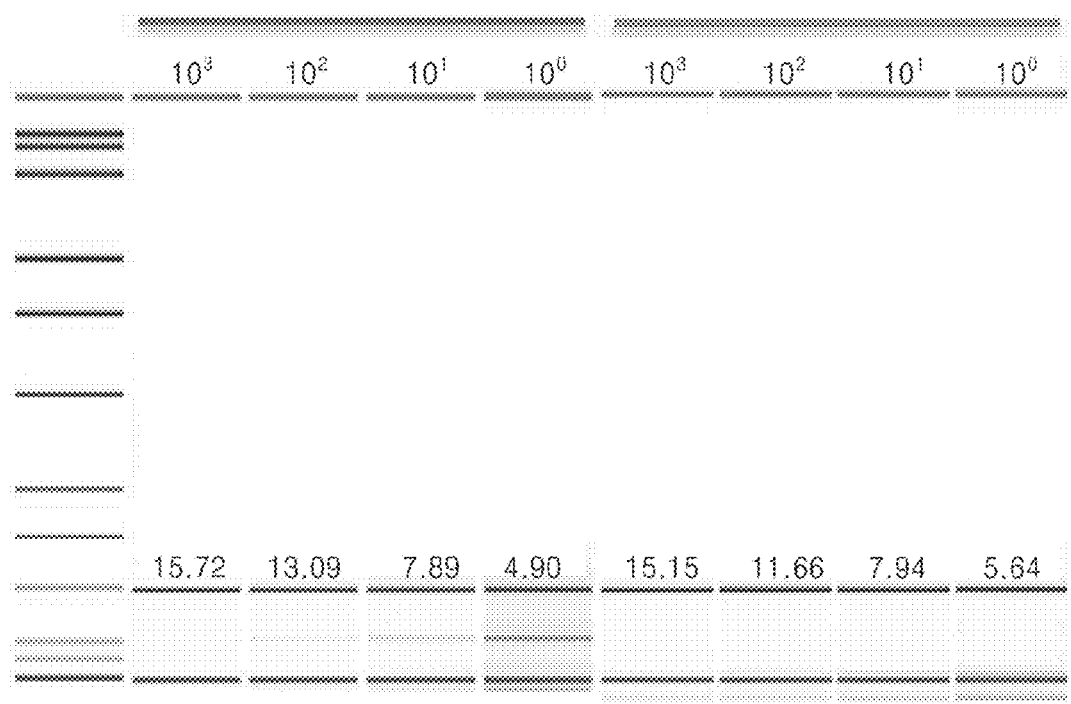
FIGS. 9(a)-(b) are images showing results of detecting a strain of Clostridium difficile by using primers for a wild-type tcdC gene (see (a)) and by using primers for a mutant tcdC gene containing Δ117 SNP that have sequences of SEQ ID NOS: 28 to 30 (see (b)), from which it was confirmed that the tcdC gene containing Δ117 SNP was specifically detectable.

The real-time PCR analysis results of the hypervirulent *Clostridium difficile* are shown in FIGS. 8 and 9.

The size of a tcdC amplicon containing Δ117 SNP which was amplified by a PCR was 86 bp. As compared to a wild-type tcdC not containing Δ117 SNP, at least one copy of the tcdC containing Δ117 SNP was specifically detectable using the primer set having the sequences of SEQ ID NOS: 13 and 14. Therefore, a hypervirulent *Clostridium difficile* strain is detectable with high sensitivity within a short period of time.

EXAMPLE 6

This example demonstrates multiplex PCR performance for detecting *Clostridium difficile*.

A multiplex PCR for detecting at least one target nucleic acid sequence by using at least one primer set (e.g., at least two, at least three, at least four, or at least five primer sets) in combination was performed in combinations as shown in Table 1 below.

TABLE 1

| NO. | C. difficile | Toxin A | Toxin B | Binary toxin | | hypervirulent |
|---|---|---|---|---|---|---|
| 1  | gluD | tcdA | tcdB | cdtA | —    | Δ 117 tcdC |
| 2  | gluD | tcdA | tcdB | —    | cdtB | Δ 117 tcdC |
| 3  | gluD | tcdA | tcdB | cdtA | cdtB | Δ 117 tcdC |
| 4  | gluD | tcdA | —    | cdtA | —    | Δ 117 tcdC |
| 5  | gluD | tcdA | —    | —    | cdtB | Δ 117 tcdC |
| 6  | gluD | tcdA | —    | cdtA | cdtB | Δ 117 tcdC |
| 7  | gluD | —    | tcdB | cdtA | —    | Δ 117 tcdC |
| 8  | gluD | —    | tcdB | —    | cdtB | Δ 117 tcdC |
| 9  | gluD | —    | tcdB | cdtA | cdtB | Δ 117 tcdC |
| 10 | gluD | tcdA | —    | cdtA | —    | —    |
| 11 | gluD | tcdA | —    | —    | cdtB | —    |
| 12 | gluD | tcdA | —    | cdtA | cdtB | —    |
| 13 | gluD | —    | tcdB | cdtA | —    | —    |
| 14 | gluD | —    | tcdB | —    | cdtB | —    |
| 15 | gluD | —    | tcdB | cdtA | cdtB | —    |
| 16 | gluD | tcdA | —    | —    | —    | —    |
| 17 | gluD | —    | tcdB | —    | —    | —    |
| 18 | gluD | —    | —    | cdtA | —    | —    |
| 19 | gluD | —    | —    | —    | cdtB | —    |
| 20 | gluD | —    | —    | cdtA | cdtB | —    |
| 21 | gluD | —    | —    | cdtA | —    | Δ 117 tcdC |
| 22 | gluD | —    | —    | —    | cdtB | Δ 117 tcdC |

As described above, according to the one or more of the above embodiments of the present invention, in a composition or kit for detecting a strain of *Clostridium difficile*, the strain of *Clostridium difficile* may be specifically detected using a primer set for a gluD gene with little variation. In addition, the composition or kit may be effectively used in a method of specifically detecting a virulent or hypervirulent *Clostridium difficile* strain by using a primer set for a virulent gene with high accuracy and sensitivity within a short period of time.

In addition, according to a method of detecting a strain of *Clostridium difficile*, the *Clostridium difficile* strain may be specifically detected using a primer set for a gluD gene with little variation. Moreover, the method may be effectively used to specifically detect a virulent or hypervirulent *Clostridium difficile* strain by using a primer set for a virulent gene with high accuracy and sensitivity within a short period of time.

It should be understood that the exemplary embodiments described therein should be considered in a descriptive sense only and not for purposes of limitation. Descriptions of features or aspects within each embodiment should typically be considered as available for other similar features or aspects in other embodiments.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method of detecting a strain of *Clostridium difficile* in a sample, the method comprising:
   hybridizing a target nucleic acid sequence from the sample with at least one primer set selected from
   (a) a primer set comprising (i) a primer comprising SEQ ID NO: 1 and (ii) a primer comprising SEQ ID NO: 2; and
   (b) a primer set comprising (i) a primer comprising SEQ ID NO: 4 and (ii) a primer comprising SEQ ID NO: 5;
   hybridizing a target nucleic acid sequence from the sample with at least one primer set selected from
   (a) a primer set comprising (i) a primer comprising of SEQ ID NO: 7 and (ii) a primer comprising SEQ ID NO: 8;
   (b) a primer set comprising (i) a primer comprising of SEQ ID NO: 22 and (ii) a primer comprising SEQ ID NO: 23; and
   (c) a primer set comprising (i) a primer comprising of SEQ ID NO: 25 and (ii) a primer comprising SEQ ID NO: 26;
   amplifying the target nucleic acid sequence; and
   detecting the amplified target nucleic acid sequence;
   wherein detection of the amplified target nucleic acid sequence indicates the presence of a strain of *Clostridium difficile* in the sample.

2. The method of claim 1, further comprising hybridizing a target nucleic acid sequence from the sample with a primer set comprising (i) a primer comprising SEQ ID NO: 14 and (ii) a primer comprising SEQ ID NO: 15.

3. The method of claim 2, further comprising hybridizing the amplified target nucleic acid sequence with a probe comprising the nucleotide sequence of SEQ ID NO: 16.

4. The method of claim 1, further comprising hybridizing a target nucleic acid sequence from the sample with a primer set comprising (i) a primer comprising SEQ ID NO: 28 and (ii) a primer comprising SEQ ID NO: 29.

5. The method of claim 4, further comprising hybridizing the amplified target nucleic acid sequence with a probe comprising the nucleotide sequence of SEQ ID NO: 30.

6. The method of claim 1, further comprising hybridizing the amplified target nucleic acid sequence with a probe comprising the nucleotide sequence of SEQ ID NO: 3 or 6.

7. The method of claim 1, further comprising hybridizing the amplified target nucleic acid sequence with a probe comprising at least one nucleotide sequence selected from the group consisting of sequences of SEQ ID NOS: 9, 24, and 27.

8. The method of claim 1, wherein the sample comprises an excrement sample, a sample collected with a cotton swab, a body fluid, or a tissue section.

9. The method of claim 1, wherein the amplifying is performed by a multiplex PCR.

10. The method of claim 1, wherein the target nucleic acid sequence that is amplified by the primer set has a size of about 40 by to 100 bp.

11. The method of claim 1, wherein detecting the amplified nucleic acid is performed in real time.

* * * * *